United States Patent [19]

Dougherty et al.

[11] 4,299,691
[45] Nov. 10, 1981

[54] REMOVAL OF PHENOLS FROM PHENOL-CONTAINING STREAMS

[75] Inventors: Herbert W. Dougherty, Cranford; Richard H. Schlosberg, New Providence, both of N.J.

[73] Assignee: Exxon Research & Engineering Co., Florham Park, N.J.

[21] Appl. No.: 204,309

[22] Filed: Nov. 5, 1980

[51] Int. Cl.$^3$ ............................................. C10G 29/16
[52] U.S. Cl. .................................................... 208/263
[58] Field of Search ......................................... 208/263

[56] References Cited

U.S. PATENT DOCUMENTS

| | | | |
|---|---|---|---|
| 1,819,687 | 8/1931 | Miller | 568/761 |
| 2,605,212 | 7/1952 | Lobban | 208/263 |
| 2,660,600 | 11/1953 | Bowman | 208/263 |
| 2,773,806 | 12/1956 | Kline et al. | 208/263 |
| 2,966,456 | 12/1960 | Honeycutt | 208/263 |
| 3,457,165 | 7/1969 | Urban | 208/263 |
| 4,256,568 | 3/1981 | Schlosberg et al. | 208/263 |

FOREIGN PATENT DOCUMENTS

| | | | |
|---|---|---|---|
| 866064 | 8/1978 | Belgium | 208/263 |
| 838900 | 3/1939 | France | 208/263 |
| 494450 | 10/1938 | United Kingdom | 208/263 |
| 496779 | 12/1938 | United Kingdom | 208/263 |

OTHER PUBLICATIONS

Gardner, et al., "Magnesium Hydroxide in the Petroleum Industry", Ind. Eng. Chem. 24, 1141-1146 (1932).
Yohe, et al., "Reaction of Coal with Oxygen in the Presence of Aqueous Sodium Hydroxide", J. Am. Chem. Soc. 69, 2644-2648 (1947).
Blom, et al., "Chemical Structure and Properties of Coal XVIII", Fuel, 36, 135-153 (1957).
Sternberg, et al., "Solubilization of Coals by Reductive Alkylation," Fuel, 53, 172-175 (1974).
McKillop, et al., "The Use of Phase-Transfer Catalysis for the Synthesis of Phenol Ethers," Tetrahedron, 30, 1379-1382 (1974).

Primary Examiner—Delbert E. Gantz
Assistant Examiner—Olik Chaudhuri
Attorney, Agent, or Firm—Henry E. Naylor

[57] ABSTRACT

Phenols are separated from phenol-containing hydrocarbonaceous streams by use of multivalent metal oxides and/or hydroxides whereupon the resulting hydroxy metal phenate is reacted with one or more alcohols selected from the group consisting of the $C_1$ to $C_{10}$ aliphatic primary alcohols and the $C_7$ to $C_{16}$ arylalkyl primary alcohols.

36 Claims, No Drawings

4,299,691

REMOVAL OF PHENOLS FROM PHENOL-CONTAINING STREAMS

BACKGROUND OF THE INVENTION

The present invention relates to the removal of phenols from phenol-containing hydrocarbonaceous streams by use of multivalent metal oxides and/or hydroxides whereupon the resulting hydroxy metal-phenate is treated with an alcohol, such as $C_1$ to $C_{10}$ aliphatic primary alcohol, to recover the phenol and to regenerate the alcohol and an oxide of the multivalent metal.

DESCRIPTION OF THE PRIOR ART

The presence of phenols in various hydrocarbonaceous streams is troublesome. For example, the presence of phenols in liquids produced from coal causes instability of these liquids over a period of time by increasing the viscosity, the color intensity, and causing separation of resinous materials. Moreover, without extensive hydrotreatment, coal liquids are generally not compatible with petroleum liquids of comparable boiling point. Thus, solids separation caused largely by high concentrations of phenols, leads to severe operability problems for coal/petroleum liquid blends. Also, hydrodesulfurization and hydrodenitrogenation of coal liquids are required prior to reforming into motor gasoline. These steps require a very large consumption of hydrogen for phenol-rich coal liquids because of the extensive deoxygenation of phenols to water.

Various methods of removing these troublesome phenols from hydrocarbonaceous streams are taught in the art. For example, it is taught that weakly acid-reacting organic substances such as phenols can be removed from hydrocarbonaceous streams by use of alkali metal or alkaline-earth metal oxides or hydroxides. It is also taught that the phenols react with these oxides or hydroxides resulting in the formation of phenoxide salts which can be easily separated from the purified stream. Further, it is known that certain phenoxide salts, such as calcium phenoxide, can be heated in the presence of carbon dioxide to yield phenols and calcium carbonate.

Another method taught for separating phenols from hydrocarbonaceous streams is to wash the stream with large quantities of water or aqueous caustic solutions such as sodium or potassium hydroxide.

Still another method for separating such phenols is taught in copending U.S. Pat. application Ser. No. 95,640, filed Nov. 19, 1979 and allowed Aug. 7, 1980 and incorporated herein by reference. That copending application teaches the treatment of phenol-containing streams with a multivalent metal oxide and/or hydroxide. The resulting hydroxy metal phenate is then pyrolyzed to recover the phenols and an oxide of the multivalent metal.

Although such methods are practiced on a commercial scale in various industries, there is still a need to develop a process for removing, from hydrocarbonaceous streams, troublesome phenols and recovering the phenols in a more efficient and inexpensive way.

SUMMARY OF THE INVENTION

In accordance with the present invention phenols are removed from phenol-containing hydrocarbonaceous streams and the phenols are regenerated by a process which comprises: (a) contacting the stream with a multivalent metal composition selected from the group consisting of one or more oxides and/or hydroxides of multivalent metals capable of forming a hydroxy metal phenate with the phenols of the stream, wherein the stream is contacted at a temperature below the decomposition temperature of the hydroxy metal phenate; (b) separating the hydroxy metal phenate from the stream; and (c) reacting the hydroxy metal phenate with one or more alcohols selected from the group consisting of $C_1$ to $C_{10}$ aliphatic primary alcohols and $C_7$ to $C_{16}$ arylalkyl alcohols, thereby generating phenols and a hydroxy-metal alcoholate.

In a preferred embodiment of the present invention, enough multivalent metal composition is employed so that at least 15 wt. % of the total phenols are removed from the stream.

In other preferred embodiments of the present invention, the phenol-containing hydrocarbonaceous stream is a coal liquid and the multivalent metal is selected from the group consisting of strontium, barium, calcium and nickel wherein the nickel has a valence of $+3$.

In still another preferred embodiment of the present invention, the hydroxy metal alcoholate is heated to above its decomposition temperature, thereby generating a multivalent metal oxide and the alcohol which was used for reacting with the hydroxy metal phenate.

DETAILED DESCRIPTION OF THE INVENTION

Phenol-containing hydrocarbonaceous streams which can be treated according to this invention include, but are not limited to, those streams resulting from the processing of coal, petroleum, and those existing as impurities in such parent streams as linear paraffins.

The term phenol-containing hydrocarbonaceous stream means a hydrocarbonaceous stream containing measurable amounts of phenol compounds in which one or more hydroxyl groups are attached to an aromatic ring and where the aromatic ring may also contain a heteroatom (e.g. nitrogen in a pyridine ring). Non-limiting examples of such phenol compounds include phenol itself (also known as benzophenol), the cresols, xylenols, recorcinol, naphthols, 8-hydroxyquinoline and 4-hydroxyquinoline. The phenol-containing hydrocarbonaceous stream, exclusive of the phenol compounds, also contains at least 25 wt. % of compounds containing carbon and hydrogen, though other atoms (e.g. nitrogen, oxygen, sulfur) may also be present.

The present invention is not dependent on the method of producing the phenol-containing hydrocarbonaceous stream. For example, any coal liquid containing phenols can be treated regardless of the method of producing the coal liquid. Non-limiting examples of processes for producing coal liquids include pyrolysis, solvent refining, direct hydrogenation with or without a catalyst, catalytic or noncatalytic hydrogenation in the presence of a non-hydrogen donor solvent and catalytic or non-catalytic liquefaction by a hydrogen donor solvent method.

Although not wishing to be limited hereby, one preferred method for obtaining coal-liquids is the Exxon Donor Solvent (EDS) process for the liquefaction of coal and described in U.S. Pat. No. 3,617,513 incorporated herein by reference. Briefly stated, the EDS process involves the formation of a slurry of coal in a hydrogen-donor solvent, such as tetralin, maintained at elevated temperatures of about 260° C. to 370° C. under agitation. Holding the coal at these temperatures causes the coal to disintegrate and dissolve without the breaking of a significant number of coal covalent bonds thereby assuring only a limited amount of free radical formation. The slurry is held at these temperatures, under agitation, until the convertible portions of the coal are substantially uniformly dispersed in the hydrogen-donor solvent. When suitable dispersion is indicated, for example, by viscosity measurements conducted on the slurry, the temperature of the slurry is increased to bond-breaking or depolymerization temperatures above about 370° C. under a pressure effective to maintain the dispersant slurry substantially in the liquid phase, generally about 350 p.s.i.g. to 3500 p.s.i.g. In this second temperature stage, the dissolved coal particles are well dispersed in the hydrogen-donor solvent and the chance of a hydrogen-donor stabilization of free radicals generated by bond breaking is maximized. At the same time, the chance for free radicals to combine with one another to produce undesirable molecules is minimized. The dispersed slurry is maintained at the elevated temperatures above about 370° C. until a predetermined conversion of the coal is obtained. The liquid, which contain phenols, is then distilled and hydrogenated, the gases drawn off, and the bottoms removed for coking and gasification.

In accordance with the present invention, the phenol-containing stream is treated with one or more multivalent metal oxides and/or hydroxides capable of forming a hydroxy metal phenate with the phenols. The stream is contacted at a temperature below the decomposition temperature of the resulting hydroxy metal phenate; generally from about room temperature (25° C.) to the decomposition temperature of the hydroxy metal phenate. For example, when calcium is the multivalent metal of the oxides and/or hydroxides used herein, the decomposition of its resulting hydroxy calcium phenate is about 490° C. The decomposition temperature of any resulting hydroxy metal phenate can be easily determined by one having ordinary skill in the art and further elaboration is therefore not deemed necessary.

Preferred multivalent metals suitable for use herein include calcium, barium, strontium and nickel. Preferred is calcium.

The amount of multivalent metal composition needed in the practice of the invention is dependent on the amount of multivalent metal required to react with a predetermined amount of the phenols in the stream. Although it may be desirable to remove as much of the phenols from the stream as possible, one may only wish to remove a certain minimum amount based on economic considerations.

The concentration of phenols in the hydrocarbonaceous stream can be determined by conventional analytical methods such as non-aqueous titration. The amount of multivalent metal needed to remove a predetermined amount of phenols can be expressed as the mol ratio of metal (in the oxide and/or hydroxide) to phenolic-oxygen (in the feed stream). The preferred mol ratio of metal to phenolic-oxygen needed herein is that ratio which, when the metal oxides and/or hydroxides are contacted with the stream, will assure the removal of at least about 15 wt. % of the phenols from the feed stream at a temperature of about 25° C. for a contact time of about 90 minutes. The wt. % of phenol removal is based on the total weight of phenols in the stream.

It will be noted that because the activity of some metals is greater than that of other metals under a given set of conditions, less of the more active metal, for a given amount of phenols in the feed stream is required to remove a predetermined amount of the phenols from the stream. For example, at a temperature of 25° C. and a contact time of 90 minutes, 17 wt. % of phenols are removed from a phenol-containing coal liquid using zinc hydroxide at a metal to oxygen mol ratio of 1.0 whereas at the same temperature and metal to oxygen mol ratio, about 72 wt. % of phenols are removed from the same coal liquid when calcium hydroxide is used. The relative activity of one metal to another is known in the art and the ratio of any given metal to oxygen can be determined by either routine experimentation or calculation by one having ordinary skill in the art.

In order to achieve a high percentage of phenol removal with any metal, a multistage process can be used. For example, at a calcium to oxygen mol ratio of 0.2, a contact time of 90 minutes, and at a temperature of 25° C., 48 wt. % removal of phenols from a coal liquid is achieved. If the treated coal liquid is contacted a second time under the same mol ratio, time, and temperature conditions as the first stage, an overall 77 wt. % removal of phenols is achieved. Therefore, it may be desirable to contact the liquid from a previous stage many times over to effect substantially total removal of the phenols from the stream. For example, after initial contact of the stream with the multivalent metal composition, the treated stream is separated from the resulting hydroxy metal phenate and passed on to another stage for contact with additional multivalent metal composition. This sequence can be repeated as often as practical and desirable.

It may be desirable from an energy savings point of view that the phenol-containing hydrocarbonaceous stream be at elevated temperatures when contacted with the multivalent metal composition. In this context, elevated temperatures means temperatures greater than room temperature but lower than the decomposition temperature of the resulting hydroxy metal phenate. Generally, the phenol-containing feed stream will result from a chemical, petroleum or coal process and will exit such process at elevated temperatures whereupon it can be treated directly with the multivalent metal composition as long as the temperature of the stream is lower than the decomposition temperature of the resulting hydroxy metal phenate. Therefore, the temperature of the phenol-containing feed stream is dependent on the source and process for its production and may have to be cooled to a lower temperature before treatment.

Preferably it is desirable to treat the feed stream with the multivalent metal composition as close to the decomposition temperature of the resulting hydroxy metal phenate as possible. By doing so, the rate of reaction is increased and the addition of heat is not required to bring the feed stream up to an efficient reaction temperature. Therefore, if the feed stream exits a previous process already at elevated temperatures, and is treated according to the invention at those temperatures, an energy savings is realized because no external heat is needed for elevating the temperature of the feed stream to a more desirable reaction temperature.

After the feed stream is contacted with the multivalent metal composition, the resulting hydroxy metal phenate salt is separated from the treated stream. This hydroxy metal phenate is now reacted with one or more primary alcohols selected from the group consisting of $C_1$ to $C_{10}$ aliphatic alcohols and $C_7$ to $C_{16}$ arylalkyl alcohols. The temperature at which the alcohol is reacted with the hydroxy metal phenate is from about 25° C. to about 400° C., preferably from about 50° C. to about 300° C., more preferably from about 200° C. to about 300° C. It is preferred to dry the hydroxy metal phenate before reacting it with the alcohol.

Alcohols suitable for use herein are the $C_1$ to $C_{10}$ aliphatic primary alcohols and the $C_7$ to $C_{16}$ arylalkyl primary alcohols. Preferred are the $C_1$ to $C_4$ aliphatic primary alcohols and the $C_7$ to $C_{10}$ arylalkyl primary alcohols. Non-limiting examples of such preferred alcohols include methanol, ethanol, propanol, butanol, phenylmethanol, phenylethanol, phenylpropanol and phenylbutanol. More preferred is methanol and ethanol, and most preferred is methanol.

Although not wishing to be limited by theory, it is believed that the multivalent metals suitable for use herein form a hydroxy metal phenate with the phenol functionality contained in the hydrocarbonaceous stream. These hydroxy metal phenates can undergo intramolecular proton transfer. For example, if calcium hydroxide were used as the multivalent metal composition to remove phenols according to the present invention, it is believed the following hydroxy metal phenate and reaction would result:

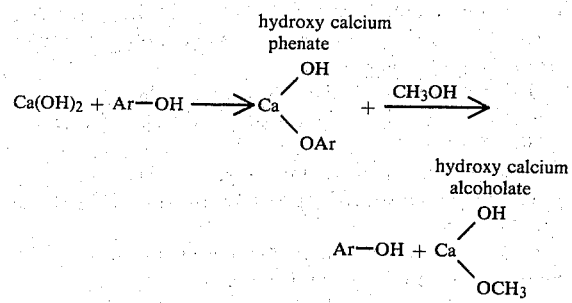

where Ar—OH represents phenolic functionality in the hydrocarbonaceous stream. As illustrated above, when the resulting hydroxy metal phenate is reacted with the primary alcohol, the phenols are regenerated and a hydroxy metal alcoholate salt results. This hydroxy metal alcoholate can be separated from the phenolic stream and heated to its decomposition temperature to regenerate the primary alcohol, used in the reaction with the hydroxy metal phenate, and to generate an oxide of the multivalent metal. The alcohol, of course, can be recycled directly to the system and the multivalent metal oxide can also be recycled directly or it can be first hydrolyzed, by any conventional means, to form the corresponding hydroxide which can then be recycled to the feed stream. One preferred method of converting the metal oxide to the corresponding hydroxide is by the introduction of stoichiometric amounts of water.

It will be noted that, if present, carboxylic compositions may also be removed from the hydrocarbonaceous stream when treated according to the present invention.

A preferred method of practicing the present invention is a continuous stirred tank reactor process which comprises contacting a phenol-containing hydrocarbonaceous feed stream with a predetermined concentration of multivalent metal oxide, and/or hydroxide composition. This multivalent metal composition can contact the hydrocarbonaceous stream as either a solid or as an aqueous slurry containing the solid multivalent metal composition. It is preferred that the hydrocarbonaceous stream be contacted with only solid particles of the multivalent metal composition so as to eliminate an aqueous phase.

As previously discussed, the amount of multivalent metal composition contacting the stream is dependent on the desired mol ratio of metal to phenolic-oxygen in the stream. For purposes of this invention, it is preferred that the mol ratio be at least that which will remove at least 15 wt. % of phenols from the stream. The multivalent metal composition and stream are preferably slurried to assure contact of the phenols with the multivalent metal composition. The phenols in the stream react with the multivalent metal composition thereby forming a hydroxy metal phenate. The hydroxy metal phenate is separated from the stream by any conventional method and the hydrocarbonaceous effluent portion of the stream is passed on for further processing, further contacting with additional multivalent metal compositions, or such treatment as hydrofining. Of course, multistage processing can be performed until the desired level of phenol removal is achieved.

Other methods which can be used in practicing the present invention are fluidized or fixed bed processes using phenol sorbent materials. Suitable phenol sorbent materials include basic ceramic sorbents such as barium titanate, calcium titanate, calcium aluminate cement, and the like.

Other conventional solid/fluid processes can also be used. Non-limiting examples of such other processes include cyclic fluid bed, tube flow reactor and moving bed processes.

The presence of the hydroxy metal phenate which is formed during the practice of this invention is supported by conventional elemental analysis. That is, the amount of carbon, hydrogen and metal for each hydroxy metal phenate can be calculated empirically then substantiated by elemental analysis data.

The following examples serve to more fully describe the present invention. It is understood that these examples in no way serve to limit the true scope of this invention, but rather, are presented for illustrative purposes.

COMPARATIVE EXAMPLES A to C

Three separate examples were run at 25° C. in an autoclave by slurrying together 10 g of hydroxy calcium phenate and 24 g of methanol for various periods of time. The resulting liquid phase was analyzed for phenols by gas chromatography and the results are set forth in Table I below. The column of Table I designated "% Phenols Generated" is the wt. % of phenols generated from the phenates, based on the total theoretical amount of phenols obtainable from the phenate.

TABLE I

| Comparative Example | Hours Run | % Phenols Generated |
|---|---|---|
| A | 3.5 | 8 |
| B | 20 | 10 |
| C | 44 | 11 |

EXAMPLE 1

10 g of hydroxy calcium phenate and 18 g of methanol were slurried together in an autoclave at 250° C. for 3 hours. The resulting liquid phase was analyzed for phenols by gas chromatography and it was found that 55 wt. % of the total theoretical amount of phenols obtainable from the hydroxy calcium phenate was obtained.

EXAMPLE 2

5 g of hydroxy calcium phenate and 25 g of ethanol were slurried together in an autoclave, at 225° C. for 3 hours. The resulting liquid phase was analyzed by gas chromatography and it was found that 72 wt. % of the total theoretical amount of phenols obtainable from the phenate was obtained.

EXAMPLE 3

280 g of a coal-derived naphtha cut, having a boiling range of about 25° C. to about 230° C. and containing about 10 to 12 wt. % phenols was slurried with 39 g of calcium hydroxide for 90 minutes at 25° C. 52.5 g of solid material resulted and was separated from the treated naphtha and dried for 20 hours at 110° C. under ½ atmosphere nitrogen pressure. This solid material was comprised of hydroxy calcium phenates and excess calcium hydroxides. 5 g of this phenate-containing material was reacted with 20 g of methanol for 3 hours at 240° C. The resulting liquid phase was analyzed by gas chromatography and it was found that 41 wt. % of the total theoretical amount of phenols obtainable from the phenate was obtained.

This example demonstrates that phenols from a hydrocarbonaceous stream, such as a coal-derived liquid, can be separated from the stream by first producing the hydroxy metal phenate salt, followed by reacting the phenate with a primary alcohol such as methanol.

COMPARATIVE EXAMPLE D 5 g of hydroxy calcium phenate was slurried in an autoclave with 25 g of isopropyl alcohol for 3 hours at 250° C. The resulting liquid phase was analyzed by gas chromotography and it was found that only 6 wt. % of the total theoretical amount of phenols obtainable from the phenate was obtained.

This example illustrates that secondary alcohols are not suitable for use in the practice of the present invention.

COMPARATIVE EXAMPLE E 5 g of hydroxy calcium phenate was slurried in an autoclave with 26 g of cyclohexanol for 3 hours at 250° C. The resulting liquid phase was analyzed by gas chromatography and it was found that less than 1 wt. % of the total theoretical amount of phenols obtainable from the phenate was obtained.

This example illustrates that alicyclic alcohols are not suitable for use herein.

COMPARATIVE EXAMPLE F 10 g of sodium phenate and 24 g of methanol were slurried together in an autoclave for 3 hours at 25° C. The resulting liquid phase was analyzed by gas chromatography and it was found that about 1 wt. % of the total theoretical amount of phenols obtainable from the phenate was obtained.

COMPARATIVE EXAMPLE G 5 g of sodium phenate and 25 g of methanol were slurried together in an autoclave for 3 hours at 250° C. The resulting liquid phase was analyzed by gas chromatography and it was found that about 9 wt. % of the total theoretical amount of phenols obtainable from the phenate was obtained.

Comparative examples F and G illustrate that phenates of monovalent metals, such as sodium, are not suitable for use in the practice of the present invention.

What is claimed is:

1. A process for separating phenols from a phenol-containing coal liquid and regenerating the phenols, the process which comprises:
   (a) contacting the coal liquid with a multivalent metal composition selected from the group consisting of oxides and/or hydroxides of one or more multivalent metals capable of forming hydroxy metal phenates with the phenols of the stream, wherein said contacting is performed at temperatures lower than the decomposition temperature of the hydroxy metal phenates;
   (b) separating the hydroxy metal phenates from the treated stream; and
   (c) reacting the hydroxy metal phenates, at a temperature from about 50° C. to about 400° C., with one or more alcohols selected from the group consisting of the $C_1$ to $C_{10}$ aliphatic primary alcohols and the $C_7$ to $C_{16}$ arylalkyl primary alcohols, thereby forming phenols and hydroxy metal alcoholates.

2. The process of claim 1 wherein the mol ratio of multivalent metal to phenolic oxygen in the coal liquid is such that at least 15 wt. % of the phenols are removed from the coal liquid.

3. The process of claim 1 wherein the multivalent metal is selected from the group consisting of Ca, Ba, Sr and $Ni^{+++}$.

4. The process of claim 2 wherein the multivalent metal is selected from the group consisting of Ca, Ba, Sr and $Ni^{+++}$.

5. The process of claim 4 wherein the multivalent metal composition is a hydroxide.

6. The process of claim 5 wherein the multivalent metal composition is calcium hydroxide.

7. The process of claim 1 wherein the alcohol is selected from the group consisting of $C_1$ to $C_4$ aliphatic primary alcohols and $C_7$ to $C_{10}$ arylalkyl primary alcohols.

8. The process of claim 6 wherein the alcohol is selected from the group consisting of $C_1$ to $C_4$ aliphatic primary alcohols and $C_7$ to $C_{10}$ arylalkyl primary alcohols.

9. The process of claim 7 wherein the alcohol is methanol or ethanol.

10. The process of claim 8 wherein the alcohol is methanol or ethanol.

11. A process for separating phenols from a phenol-containing coal liquid and regenerating the phenols, the process which comprises:
    (a) contacting the coal liquid with a multivalent metal composition selected from the group consisting of oxides and/or hydroxides of one or more multivalent metals capable of forming hydroxy metal phenates with phenols of the stream, wherein said contacting is performed at temperatures lower than the decomposition temperature of the hydroxy metal phenates;
    (b) separating the hydroxy metal phenates from the treated stream;
    (c) reacting the hydroxy metal phenates, at a temperature from about 50° C. to about 400° C., with one or more alcohols selected from the group consisting of the $C_1$ to $C_{10}$ aliphatic primary alcohols and the $C_7$ to $C_{16}$ arylalkyl primary alcohols, thereby forming phenols and hydroxy metal alcoholates; and (d) heating the hydroxy metal alcoholates to their decomposition temperature, thereby forming the primary alcohol(s) and oxides of the multivalent metal.

12. The process of claim 11 wherein the mol ratio of multivalent metal to phenolic oxygen in the coal liquid is such that at least 15 wt. % of the phenols are removed from the coal liquid.

13. The process of claim 11 wherein the multivalent metal is selected from the group consisting of Ca, Ba, Sr and $Ni^{+++}$.

14. The process of claim 12 wherein the multivalent metal is selected from the group consisting of Ca, Ba, Sr, and $Ni^{+++}$.

15. The process of claim 14 wherein the multivalent metal composition is a hydroxide.

16. The process of claim 15 wherein the multivalent metal composition is calcium hydroxide.

17. The process of claim 11 wherein the process is continuous and the resulting multivalent metal oxides are recycled to the coal liquid.

18. The process of claim 17 wherein the resulting multivalent metal oxides are first hydrolyzed to the corresponding hydroxides before being recycled to the coal liquid.

19. The process of claim 1 wherein the coal liquid contains a stoichiometric amount of water to hydrolyze any multivalent oxides to hydroxides.

20. The process of claim 16 wherein the resulting multivalent metal oxides are first hydrolyzed to the corresponding hydroxides before being recycled to the feed coal liquid.

21. The process of claim 11 wherein the alcohol is selected from the group consisting of $C_1$ to $C_4$ aliphatic primary alcohols and $C_7$ to $C_{10}$ arylalkyl primary alcohols.

22. The process of claim 20 wherein the alcohol is selected from the group consisting of $C_1$ to $C_4$ aliphatic primary alcohols and $C_7$ to $C_{10}$ arylalkyl primary alcohols.

23. The process of claim 21 wherein the alcohol is methanol or ethanol.

24. The process of claim 22 wherein the alcohol is methanol or ethanol.

25. A process for removing phenols from a phenol-containing hydrocarbonaceous stream and regenerating the phenols, the process comprising:

(a) contacting the stream with a multivalent metal composition selected from the group consisting of oxides and/or hydroxides of one or more multivalent metals capable of forming a hydroxy metal phenate with the phenols of the stream, wherein said contacting is performed at temperatures lower than the decomposition temperature of the hydroxy metal phenate;

(b) separating the hydroxy metal phenate from the treated stream; and (c) reacting the hydroxy metal phenates, at a temperature from about 50° C. to about 400° C., with one or more alcohols selected from the group consisting of the $C_1$ to $C_{10}$ aliphatic primary alcohols and the $C_7$ to $C_{16}$ arylalkyl primary alcohols, thereby forming phenols and hydroxy metal alcoholates.

26. The process of claim 25 wherein the mol ratio of multivalent metal to phenolic oxygen in the stream is such that at least 15 wt. % of the phenols are removed from the stream.

27. The process of claim 25 wherein the multivalent metal is selected from the group consisting of Ca, Ba, Sr and $Ni^{+++}$.

28. The process of claim 26 wherein the multivalent metal is selected from the group consisting of Ca, Ba, Sr and $Ni^{+++}$.

29. The process of claim 27 wherein the multivalent metal composition is a hydroxide.

30. The process of claim 28 wherein the multivalent metal composition is calcium hydroxide.

31. The process of claim 25 wherein the resulting hydroxy metal alcoholates are heated to their decomposition temperature, thereby forming primary alcohols and oxides of the multivalent metal.

32. The process of claim 31 wherein the process is continuous and the resulting multivalent metal oxides are recycled to the hydrocarbonaceous stream.

33. The process of claim 32 wherein the resulting multivalent metal oxides are first hydrolyzed to the corresponding hydroxides before being recycled to the hydrocarbonaceous stream.

34. The process of claim 25 wherein the alcohol is selected from the group consisting of the $C_1$ to $C_4$ aliphatic primary alcohols and the $C_7$ to $C_{10}$ arylalkyl primary alcohols.

35. The process of claim 33 wherein the alcohol is selected from the group consisting of the $C_1$ to $C_4$ aliphatic primary alcohols and the $C_7$ to $C_{10}$ arylalkyl primary alcohols.

36. The process of claim 35 wherein the alcohol is methanol or ethanol.

* * * * *